United States Patent
Hoffman

(12) 
(10) Patent No.: US 6,479,824 B1
(45) Date of Patent: Nov. 12, 2002

(54) SCINTILLATOR ARRAYS FOR CT IMAGING AND OTHER APPLICATIONS

(75) Inventor: David M. Hoffman, New Berlin, WI (US)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 0 days.

(21) Appl. No.: 09/708,760

(22) Filed: Nov. 8, 2000

(51) Int. Cl.$^7$ ................................................. G01T 1/20
(52) U.S. Cl. ...................................................... 250/367
(58) Field of Search ................................ 250/367, 368, 250/366; 378/19

(56) References Cited

U.S. PATENT DOCUMENTS

| | | | |
|---|---|---|---|
| 3,749,920 A | * 7/1973 | Sheldon | 250/213 VT |
| 4,069,355 A | * 1/1978 | Lubowski et al. | 427/70 |
| 4,316,092 A | * 2/1982 | Rabatin | 250/483.1 |
| 4,491,732 A | 1/1985 | Pritzkow et al. | |
| 4,560,877 A | 12/1985 | Hoffman | |
| 4,563,584 A | 1/1986 | Hoffman et al. | |
| 4,720,426 A | * 1/1988 | Englert et al. | 428/344 |
| 5,440,129 A | * 8/1995 | Schmidt | 250/366 |
| 5,519,227 A | * 5/1996 | Karellas | 250/483.1 |
| 6,013,723 A | * 1/2000 | Akao | 524/577 |
| 6,087,665 A | 7/2000 | Hoffman et al. | |
| 6,173,031 B1 | 1/2001 | Hoffman et al. | |
| 6,252,231 B1 | * 6/2001 | Harootian | 250/368 |

FOREIGN PATENT DOCUMENTS

| | | |
|---|---|---|
| DE | 19839786 A1 | 5/1999 |
| DE | 19849772 A1 | 5/1999 |

* cited by examiner

*Primary Examiner*—Constantine Hannaher
*Assistant Examiner*—Shun Lee
(74) *Attorney, Agent, or Firm*—Carl B. Horton, Esq.; Armstrong Teasdale LLP

(57) ABSTRACT

One embodiment of the present invention is a detector for detecting x-rays of an imaging system. The detector has a plurality of photodetectors; and a plurality of scintillator elements optically coupled to the plurality of photodetectors. The scintillator elements have sides separated from adjacent scintillator elements by gaps; and a cast reflector mixture in the gaps between the sides of the scintillator elements. The cast reflector mixture include a first powdered material having a higher Z and a higher density than titanium dioxide, and a refractivity index sufficient to effectively scatter and reflect light within the cast reflector mixture.

42 Claims, 2 Drawing Sheets

US 6,479,824 B1

SCINTILLATOR ARRAYS FOR CT IMAGING AND OTHER APPLICATIONS

BACKGROUND OF THE INVENTION

This invention relates generally to methods and apparatus for detecting radiation in CT imaging and other radiation imaging systems, and more particularly to scintillator arrays having a cast reflector mixture that includes at least one filler material selected to enhance performance.

In at least some computed tomography (CT) imaging system configurations, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. X-ray sources typically include x-ray tubes, which emit the x-ray beam at a focal spot. X-ray detectors typically include a collimator for collimating x-ray beams received at the detector, a scintillator adjacent the collimator, and photodetectors adjacent the scintillator.

One or more rows of scintillator cells are provided in a detector array configured to acquire projection data from which one or more image slices of an object are reconstructed. One known detector array includes a two-dimensional array of scintillator cells, with each scintillator cell having an associated photodetector. An epoxy material is used to cast the scintillator cells into a block having specified dimensions for easier handling. To maximize reflectivity and to prevent cross-talk between adjacent detector cells, the cast reflector mixture includes a material having a high refractive index, such as $TiO_2$. Thus, light generated in the scintillating material by impinging x-rays is confined to the detector cell in which it is generated. However, neither the epoxy, the $TiO_2$, nor their mixture are particularly absorptive of x-rays. Thus, neither the photodetectors nor the cast reflector mixture itself is protected from damage caused by impinging x-rays.

In one known cast reflector mixture, a small amount of an oxide of chromium is also incorporated in the cast reflector mixture to further reduce cross talk between cells. However, inclusion of this material reduces the efficiency of the detector, because the absorbed portion of the generated visible light is never detected by the photodetectors.

In one known CT imaging system, a post-patient collimator is used. This collimator comprises tungsten wires perpendicular to a series of plates that are suspended above cast gaps between scintillator elements. Such post-patient collimators are used to prevent x-rays from significantly penetrating cast reflector mixture in gaps between scintillator elements, from entering the sides of scintillator elements that are not directly facing the x-ray source, and from entering photodetectors associated with scintillator elements. Post-patient collimators have also been used because the focal spot of the x-ray source of the CT imaging system is not perfectly stable, and its movement would result in a change in apparent projected detector cell aspect ratio were it not for the presence of the post-patient collimator. A typical post-patient collimator is required to be about 0.008" thick at the gaps between scintillator elements because of alignment tolerances of the CT imaging system. This thickness is high enough to reduce the quantum efficiency of the scintillator elements because of excess shadowing.

It would therefore be desirable to provide a detector that inherently provides protection for photodetectors and cast reflector mixture. It would also be desirable if the detector had improved x-ray quantum efficiency. Ideally, it would also be desirable if the detector provided reduced manufacturing costs by eliminating the need for a post-patient collimator in front of the detector array.

BRIEF SUMMARY OF THE INVENTION

There is therefore provided, in one embodiment, a detector for detecting x-rays of an imaging system. The detector has a plurality of photodetectors; and a plurality of scintillator elements optically coupled to the plurality of photodetectors. The scintillator elements have sides separated from adjacent scintillator elements by gaps; and a cast reflector mixture in the gaps between the sides of the scintillator elements. The cast reflector mixture include a first powdered material having a higher Z and a higher density than titanium dioxide, and a refractivity index sufficient to effectively scatter and reflect light within the cast reflector mixture.

The above-described embodiment inherently provides protection for photodetectors and cast reflector mixture, and is capable of providing improved x-ray quantum efficiency and of eliminating the need for a post-patient collimator in front of the detector array.

DETAILED DESCRIPTION OF THE INVENTION

Figure 1:
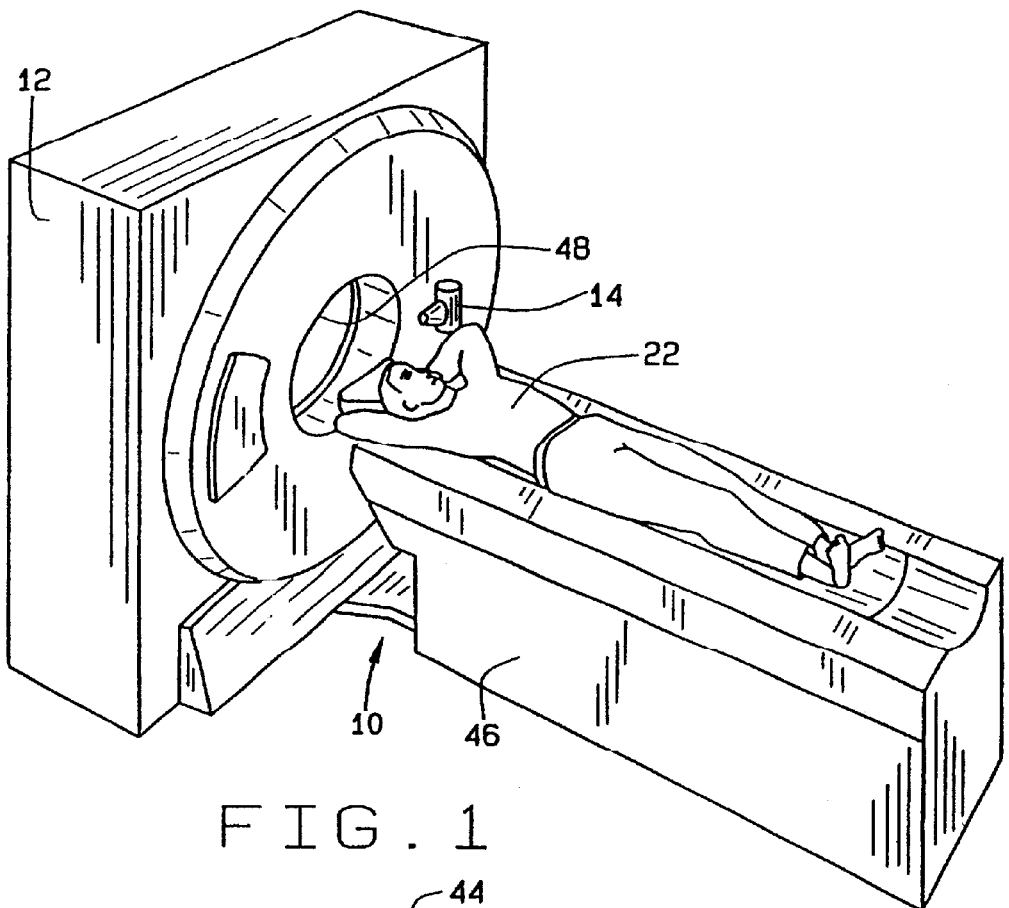
FIG. 1 is a pictorial view of a CT imaging system.
Figure 2:
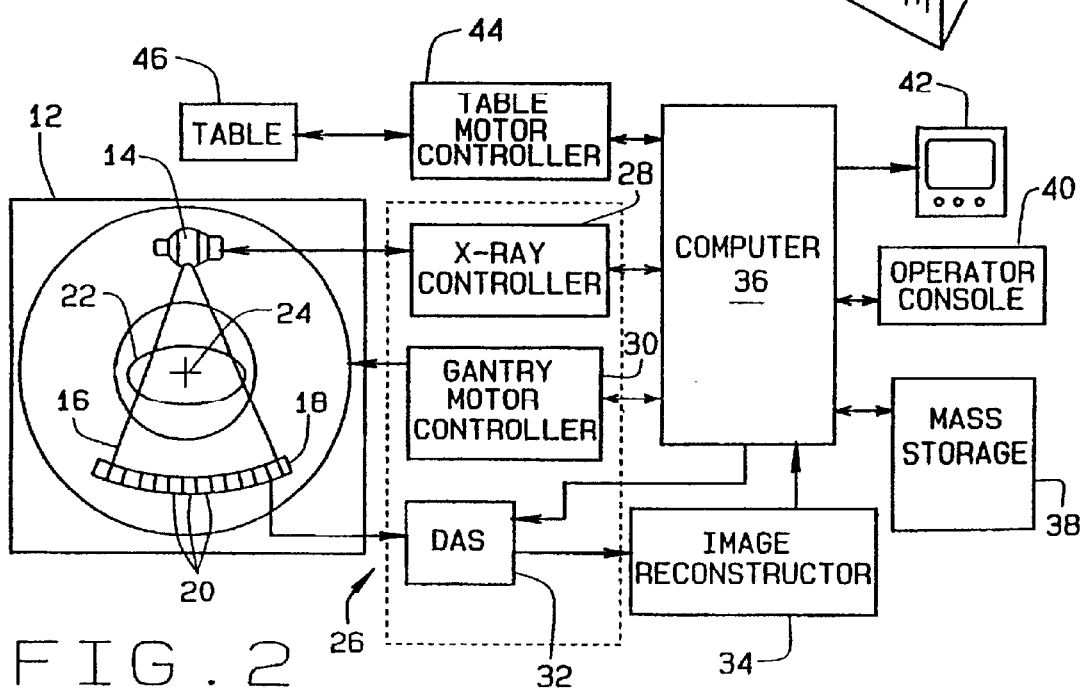
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through an object, such as a medical patient 22. Each detector element 20 produces an electrical signal that represents the intensity of an impinging x-ray beam and hence the attenuation of the beam as it passes through object or patient 22. During a scan to acquire x-ray projection data, gantry 12 and the components mounted thereon rotate about a center of rotation 24. In one embodiment, and as shown in FIG. 2, detector elements 20 are arranged in one row so that projection data corresponding to a single image slice is acquired during a scan. In another embodiment, detector elements 20 are arranged in a plurality of parallel rows, so that projection data corresponding to a plurality of parallel slices can be acquired simultaneously during a scan.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

Figure 3:
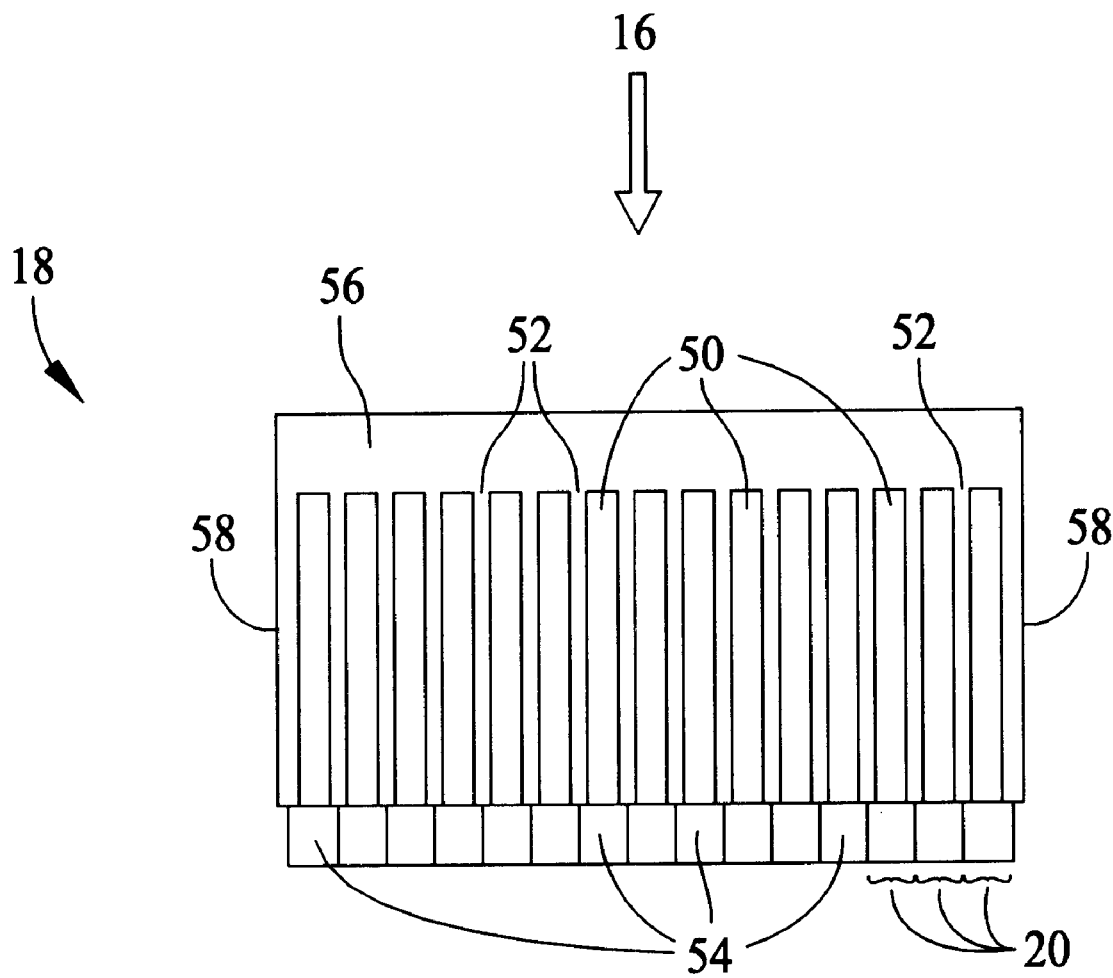
FIG. 3 is drawing representing a cross-section through an embodiment of a detector array of the present invention.

As explained above, each detector element 20 of array 18 produces a separate electrical signal that is a measurement of the beam attenuation at the detector location. Particularly, and referring to FIG. 3, each x-ray detector element 20 includes a scintillator element 50, and sides of adjacent scintillator elements 50 are separated by non-scintillating gaps 52. In addition, although FIG. 3 depicts a cross section through a row of detector elements 20, FIG. 3 is intended to be representative of both linear and two-dimensional (e.g., rectangular) arrays of detector elements 20. When struck by x-rays, scintillator elements 50 convert at least a portion of energy of the x-rays into light that can be detected by photodetectors 54 positioned adjacent scintillator elements 50. Photodetectors 54 (for example, photodiodes or photocells) optically coupled to the backs of scintillator elements 50 generate electrical signals representative of the light output by scintillator elements 50. The attenuation measurements from all detector elements 20 in detector array 18 are acquired separately to produce a transmission profile.

In one embodiment of the present invention, a cast reflector mixture is cast in gaps 52 between adjacent scintillator elements 50. The casting compound includes a castable material such as an epoxy, and a filler material. In one embodiment, a suitable filler material comprises a first powdered material having a higher Z and a higher density than titanium dioxide, and a refractivity index sufficient to effectively scatter and reflect light within the cast reflector mixture. For example, the first powdered material has a refractivity index greater than 1.5. Additionally, in one embodiment, the cast reflector mixture comprises at least 10% by weight of the first powdered material up to a maximum dispersible amount of the first powdered material.

Examples of suitable first powdered materials are a white oxide of a metal, a white inorganic compound of a metal, and combinations thereof. Exemplary white oxides and white inorganic compounds of metals include white oxides, carbonates, and sulfates of lead, zinc, tin, antimony, bismuth, tantalum, tungsten, lanthanum, and zirconium, and combinations thereof. In yet another embodiment, the cast reflector mixture further comprises a second powdered material having a higher refractive index than the first powdered material. In one exemplary embodiment, the second powdered material has a refractivity index not less than 1.6 and the cast reflector mixture comprises at least 10% by weight of the second powdered material. In another exemplary embodiment, the cast reflector mixture comprises at least 10% by weight of the first powdered material and a maximum dispersible amount of the second powdered material. The "maximum dispersible amount" of the second powdered material is defined in a manner that takes into account the amount of the first powdered material already present and thus may be different than if the first powdered material were not present.

Suitable second powdered materials include white oxides, sulfates, and carbonates of titanium, barium, magnesium, calcium, aluminum, and strontium that have refractivity indices not less than 1.6, and combinations of these materials. For example, in one embodiment, the second powdered material is titanium dioxide ($TiO_2$).

In one embodiment, the casting compound is cast in front of 56 as well as in gaps 52 between adjacent scintillator elements 50, so that a surface of the cast reflector mixture faces x-ray source 16.

Neither $TiO_2$ nor epoxy, by itself, is particularly absorptive of x-rays. However, the higher Z, high density, high refractive index first powdered material does absorb x-rays, which protects both photodetectors 54 and the epoxy cast reflector mixture itself from x-ray damage. However, sufficient x-ray energy passes through the front, reflective cast coating 56 of detector elements 20 to allow collection of attenuation data. In addition, light produced by a scintillator element 50 is reflected back towards corresponding photodetector 54 by the reflective cast coating at the front and at the sides of element 50.

Embodiments of the present invention enable detector arrays 18 to be used without post-patient collimators because x-rays are exponentially attenuated in the cast reflector mixture around each scintillator element 50. For example, in one embodiment employing white lead oxide as a filler, 60 to 70 percent of the x-rays are absorbed by traveling 3 mm through the cast reflector mixture. This absorption effectively prevents x-rays from significantly penetrating gaps 52, from entering sides of scintillator elements 50, and from entering photodetectors 54 of scintillator elements 50. In one embodiment, for example, gaps 52 are 0.004" thick, whereas a typical post-patient collimator is required to be 0.008" thick at gaps 52 because of alignment tolerances of CT imaging system 10. The high thickness of the post-patient collimator needed because of alignment tolerances results in excess shadowing. Embodiments of the present invention provide reflective gaps 52, eliminating the need for a post-patient collimator. Without a post-patient collimator, excess shadowing is eliminated and quantum efficiency is increased.

In one embodiment of the present invention, the first powdered -material is also luminescent to x-rays. Suitable luminescent materials that also have high-Z, high density and a scattering refractive index include, for example, gadolinium oxysulfide, cadmium tungstate, calcium tungstate, bismuth germanate, yttrium gadolinium oxide, or mixtures thereof. Also in one embodiment, a light absorbing material such as a chromium oxide, carbon black, or a mixture thereof, is also used as a component of the filler. For example, the cast reflector material is a mixture of epoxy, $TiO_2$, an oxide of chromium (such as $Cr_2O_3$), and a first powdered material that is a scintillator material. These embodiments improve x-ray quantum efficiency because the powdered scintillator material emits visible light as a result of its absorption of x-rays.

In one embodiment, the filling material comprises the scintillator power in conjunction with, or in place of, the second powdered material.

An exemplary x-ray detector embodiment is made by optically coupling a plurality of scintillator elements 50 to a plurality of photodetectors 54 and casting one of the cast reflector mixtures described herein in gaps 52 between adjacent scintillator elements. Casting can occur before, after, or during the coupling of the scintillator elements to the photodetectors. In one embodiment, photodetectors 54 are optically coupled to the back of the scintillator elements 50 (i.e., a side intended for mounting away from an x-ray source 14), and a front side 56 (i.e., a side intended for mounting towards an x-ray source 14) is also coated with the cast reflector mixture. In one embodiment, sides 58 of detector array 18 are also coated with the cast reflector mixture.

It will be recognized by those skilled in the art that the present invention is applicable not only to scintillators used in CT imaging systems, but also in other systems using x-ray detector cells to acquire an image of an object. Also, scintillator elements 50 need not have uniform composition. For example, composite scintillator elements 50 (for example, laminated elements) are used in one embodiment.

While the invention has been described in terms of various specific embodiments, those skilled in the art will recognize that the invention can be practiced with modification within the spirit and scope of the claims.

What is claimed is:

1. A detector for detecting x-rays of an imaging system, said detector comprising:
    a plurality of photodetectors;
    a plurality of scintillator elements optically coupled to the plurality of photodetectors, the scintillator elements having sides separated from adjacent scintillator elements by gaps; and
    a cast reflector mixture in the gaps between the sides of the scintillator elements, said cast reflector mixture comprising a first powdered material having a higher Z and a higher density than titanium dioxide, and a refractivity index sufficient to effectively scatter and reflect light within the cast reflector mixture, and a second powdered material having higher refractivity than said first powdered material.

2. A detector in accordance with claim 1 wherein the first powdered material has a refractivity index greater than 1.5.

3. A detector in accordance with claim 2 wherein the cast reflector mixture further comprises an epoxy.

4. A detector in accordance with claim 2 wherein the cast reflector mixture comprises at least 10 percent by weight of the first powdered material.

5. A detector in accordance with claim 4 wherein the cast reflector mixture comprises a maximum dispersible amount of the first powdered material.

6. A detector in accordance with claim 4 wherein the first powdered material comprises a material selected from the group consisting of white oxides of metals, white inorganic compounds of metals, and combinations thereof.

7. A detector in accordance with claim 4 wherein the first powdered material comprises a material selected from the group consisting of white oxides, carbonates, and sulfates of lead, zinc, tin, antimony, bismuth, tantalum, tungsten, lanthanum, and zirconium, and combinations thereof.

8. A detector in accordance with claim 4 wherein the scintillator elements have a front and a back, the plurality of photodetectors are optically coupled to the back of the plurality of scintillator elements, and the cast reflector mixture covers the front of the scintillator elements.

9. A detector in accordance with claim 1 wherein the second powdered material has a refractivity index not less than 1.6.

10. A detector in accordance with claim 9 wherein the cast reflector mixture comprises at least 10% by weight of the second powdered material.

11. A detector in accordance with claim 10 wherein the cast reflector mixture comprises a maximum dispersible amount of the second powdered material, taking into account the at least 10% by weight of the first powdered material.

12. A detector in accordance with claim 10 wherein the second powdered material comprises a material selected from the group consisting of white oxides, sulfates, and carbonates of titanium, barium, magnesium, calcium, aluminum, and strontium that have refractivity indices not less than 1.6, and combinations thereof.

13. A detector in accordance with claim 12 wherein the cast reflector mixture further comprises a light absorbing powder.

14. A detector in accordance with claim 13 wherein the light absorbing powder comprises an oxide of chromium.

15. A detector in accordance with claim 13 wherein the light absorbing powder comprises carbon black.

16. A detector in accordance with claim 2 wherein the first powdered material is luminescent to x-rays.

17. A detector in accordance with claim 16 wherein the first powdered material has a refractivity index greater than 1.5.

18. A detector in accordance with claim 17 wherein the cast reflector mixture comprises at least 10% by weight of the first powdered material.

19. A detector in accordance with claim 18 wherein the first powdered material comprises a material selected from the group consisting of gadolinium oxysulfide, cadmium tungstate, calcium tungstate, bismuth germanate, yttrium gadolinium oxide, and mixtures thereof.

20. A detector in accordance with claim 18 wherein the cast reflector mixture further comprises a second powdered material having a higher refractivity index than the first powdered material.

21. A detector in accordance with claim 20 wherein the second powdered material has a refractivity index not less than 1.6.

22. A detector in accordance with claim 21 wherein the cast reflector mixture comprises at least 10% by weight of the second powdered material.

23. A detector in accordance with claim 22 wherein the second powdered material comprises a material selected from the group consisting of white oxides, sulfates, and carbonates of titanium, barium, magnesium, calcium, aluminum, and strontium that have refractivity indices not less than 1.6, and combinations thereof.

24. A detector in accordance with claim 23 wherein the cast reflector mixture further comprises a light absorbing powder.

25. A detector in accordance with claim 24 wherein the light absorbing powder comprises a material selected from the group consisting of chromium oxides and carbon black, and mixtures thereof.

26. An imaging system comprising:
    a detector array in accordance with claim 1;
    an x-ray source; and
    a rotating gantry, wherein the x-ray source and detector array are on opposite sides of the rotating gantry, the x-ray source is configured to project x-rays through an object, and the detector array is configured to sense projected x-rays that pass through the object and to produce electrical signals representing attenuation of the x-ray beam as it passes through the object.

27. An imaging system comprising:

a detector array in accordance with claim 7;

an x-ray source; and a rotating gantry, wherein the x-ray source and detector array are on opposite sides of the rotating gantry, the x-ray source is configured to project x-rays through an object, and the detector array is configured to sense projected x-rays that pass through the object and to produce electrical signals representing attenuation of the x-ray beam as it passes through the object.

28. An imaging system comprising:

a detector array in accordance with claim 10;

an x-ray source; and a rotating gantry, wherein the x-ray source and detector array are on opposite sides of the rotating gantry, the x-ray source is configured to project x-rays through an object, and the detector array is configured to sense projected x-rays that pass through the object and to produce electrical signals representing attenuation of the x-ray beam as it passes through the object.

29. An imaging system comprising:

a detector array in accordance with claim 16;

an x-ray source; and a rotating gantry, wherein the x-ray source and detector array are on opposite sides of the rotating gantry, the x-ray source is configured to project x-rays through an object, and the detector array is configured to sense projected x-rays that pass through the object and to produce electrical signals representing attenuation of the x-ray beam as it passes through the object.

30. An imaging system comprising:

a detector array in accordance with claim 22;

an x-ray source; and a rotating gantry, wherein the x-ray source and detector array are on opposite sides of the rotating gantry, the x-ray source is configured to project x-rays through an object, and the detector array is configured to sense projected x-rays that pass through the object and to produce electrical signals representing attenuation of the x-ray beam as it passes through the object.

31. A method for making an x-ray detector comprising the steps of:

optically coupling a plurality of photodetectors to a plurality of scintillator elements, the scintillator elements each having sides, a front, and a back; and casting a reflector mixture comprising a first powdered material having a higher Z and a higher density than titanium dioxide, and a refractivity index sufficient to effectively scatter and reflect light within the cast reflector mixture, and a second powdered material having a higher refractivity index than the first powdered material.

32. A method in accordance with claim 31 wherein the casting of a reflector mixture comprising a first powdered material comprises the step of casting a reflector mixture containing at least 10% by weight of a first powdered material having a refractivity index greater than 1.5.

33. A method in accordance with claim 32 wherein the first material comprises a material selected from the group consisting of white oxides, carbonates, and sulfates of lead, zinc, tin, antimony, bismuth, tantalum, tungsten, lanthanum, and zirconium, and combinations thereof.

34. A method in accordance with claim 32 wherein said step of optically coupling a plurality of photodetectors to a plurality of scintillator elements comprises optically coupling the plurality of photodetectors to the backs of the plurality of scintillator elements, and said method further comprises the step of casting the cast reflector mixture over the front of the scintillator elements.

35. A method in accordance with claim 32 wherein the cast reflector mixture further comprises a second powdered material having higher refractivity than the first powdered material.

36. A method in accordance with claim 35 wherein the second powdered material has a refractivity index not less than 1.6 and the cast reflector mixture comprises at least 10% by weight of the second powdered material.

37. A method in accordance with claim 36 wherein the cast reflector mixture further comprises a light absorbing powder.

38. A method in accordance with claim 31 wherein the first powdered material is luminescent to x-rays.

39. A method in accordance with claim 38 wherein the first powdered material has a refractivity index greater than 1.5 and the cast reflector mixture comprises at least 10% by weight of the first powdered material.

40. A method in accordance with claim 39 wherein the first powered material comprises a material selected from the group consisting of gadolinium oxysulfide, cadmium tungstate, calcium tungstate, bismuth germanate, yttrium gadolinium oxide, and mixtures thereof.

41. A method in accordance with claim 31 wherein the second powdered material has a refractivity index not less than 1.6 and comprises at least 10% by weight of the second powdered material.

42. A method in accordance with claim 41 wherein the cast reflector mixture further comprises a light absorbing powder.

* * * * *